United States Patent [19]

Snyder, Jr.

[11] 4,035,421
[45] July 12, 1977

[54] N-(3,4,-DICHLOROPHENYL)-2-PHENYLE-THENESULFONAMIDE

[75] Inventor: Harry R. Snyder, Jr., Norwich, N.Y.

[73] Assignee: Morton-Norwich Products, Inc., Norwich, N.Y.

[21] Appl. No.: 668,612

[22] Filed: Mar. 19, 1976

[51] Int. Cl.² .............. C07C 143/79; A61K 31/18
[52] U.S. Cl. ................. 260/556 AR; 260/556 A; 424/321
[58] Field of Search ............... 260/556 A, 556 AR

[56] References Cited
U.S. PATENT DOCUMENTS 3,120,102  2/1964  Tull et al. .............. 260/553 D X

OTHER PUBLICATIONS

Hartig, J. Prak. Chemie 33 (3–4), pp. 215–224 (1966).

*Primary Examiner*—Daniel E. Wyman
*Assistant Examiner*—Thomas A. Waltz
*Attorney, Agent, or Firm*—Anthony J. Franze

[57] ABSTRACT

Antibacterially active N-(3,4-dichlorophenyl)-2-phenylethenesulfonamide.

1 Claim, No Drawings

N-(3,4,-DICHLOROPHENYL)-2-PHENYLE-THENESULFONAMIDE

This invention relates to chemical compounds and more particularly to the compound N-(3,4-dichlorophenyl)-2-phenylethenesulfonamide of the formula:

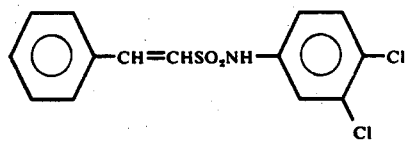

and to compositions containing it.

This compound is an effective antibacterial agent in very small amounts. It is capable of inhibiting the growth of bacteria when tested by the commonly used serial dilution technique as exemplified in the following table:

| Organism | Inhibiting Concentration µg/ml |
| --- | --- |
| S. aureus | 12.5 |
| E. coli | 12.5 |
| H. vaginalis | 50 |

In addition, this compound is active against the fungus M. canis at 10 µg/ml as determined by the standard agar plate test.

It is thus adapted to the combined in solutions, suspensions, sprays, dusts, ointments, suppositories and the like as an active ingredient to suppress or eradicate microbial growth.

The method of preparing the compound of this invention which is currently preferred consists in bringing together 3,4-dichloroaniline and 2-phenylethenesulfonyl chloride in boiling benzene. The product is isolated by diluting the benzene solution with hexane and filtering.

In order that this invention may be fully available to and understood by those skilled in the art, the following member of its manufacture is set forth:

A solution of 3,4-dichloroaniline (48.6 g, 0.3 mole) in benzene was added to a benzene solution of 2-phenylethenesulfonyl chloride (30.3 g, 0.15 mole). The resulting solution was stirred at reflux for five hours and filtered hot. The filtrate was concentrated to ⅓ volume and diluted with hexane. After chilling, the crude product crystallized to yield 43.3 g. (88%), m.p. 86°–89° C. The material was recrystallized from a benzene-hexane mixture, after treatment with charcoal, to yield 27.2 g, m.p. 92°–93° C.

Analysis Calcd. for $C_{14}H_{11}Cl_2NO_2S$: C, 51.23; H, 3.38; N, 4.27. Found: C, 51.34; H, 3.46; N, 4.18.

What is claimed is:
1. N-(3,4-dichlorophenyl)-2-phenylethenesulfonamide.